United States Patent [19]
Jörnéus

[11] Patent Number: 5,064,375
[45] Date of Patent: Nov. 12, 1991

[54] HOLDER

[75] Inventor: Lars Jörnéus, Gothenburg, Sweden

[73] Assignee: Nobelpharma AB, Goteborg, Sweden

[21] Appl. No.: 611,830

[22] Filed: Nov. 13, 1990

[30] Foreign Application Priority Data

Nov. 13, 1989 [SE] Sweden .................................. 8903797

[51] Int. Cl.⁵ ................................................ A61C 3/00
[52] U.S. Cl. ................................ 433/229; 433/116; 433/141; 433/174
[58] Field of Search ............... 433/116, 141, 173, 174, 433/114, 127, 229

[56] References Cited

U.S. PATENT DOCUMENTS

| | | | |
|---|---|---|---|
| 2,472,103 | 6/1949 | Giesen | 433/174 |
| 4,498,468 | 2/1985 | Hansson | 433/173 |
| 4,824,372 | 4/1989 | Jörneus et al. | 433/174 |

FOREIGN PATENT DOCUMENTS 2494579  5/1982  France .

Primary Examiner—Gene Mancene
Assistant Examiner—Michael Lynch
Attorney, Agent, or Firm—Pollock, Vande Sande & Priddy

[57] ABSTRACT

A holding device allows for tightening of a screw joint in a bone-anchored dental implant without imposing stress upon the tissue surrounding the implant. The device includes a first part which is rotationally locked in relation to the implant and a second part in the form of an arm which is rigidly connected to the first part, extends substantially perpendicularly thereto and is provided with a holding portion which interacts with the stationary part of the tightening tool to prevent undesirable rotary movements.

6 Claims, 2 Drawing Sheets

HOLDER

FIELD OF THE INVENTION

The present invention relates to an apparatus adapted for tightening of a screw joint in a bone-anchored dental implant without imposing on the tissue surrounding the implant.

BACKGROUND ART

It is already known to anchor permanently a dental prosthesis in the jaw with the aid of screws made of titanium implanted in the jawbone. The screws are anchored in holes in the bone so that the upper part of the screw is situated on a level with or immediately below the upper surface of the jaw bone. The screw is then covered over with a mucous membrane flap and is left unstressed for a rest period of 3-6 months in order that the bone grows onto and form a unit with the implanted screw. After the rest period, the screw is uncovered and a distance element, also preferably made of titanium, is arranged on the screw, whereupon a dental prosthesis is anchored on the distance element.

As a result of the high oral stresses during biting and chewing, dental prostheses have in general been anchored by means of a bridge construction with the aid of a number of fixtures, for example six pieces. If any of the screws comes loose, those remaining then ensure that the secure anchoring is still maintained.

In recent years, however, efforts have been made to provide secure anchoring of individual teeth. In the case of such a single-tooth replacement, one single screw is to be able to absorb all arising oral stresses such as torsion, stretching and pressure forces. Especially important in this respect is the torsional load which tends to loosen the screw joint between distance screw and screw (fixture). For single-tooth replacements which are subjected the high oral stresses, it is of course important that the design and anchoring of the screw and the distance element are the best possible in order to prevent the screw joint from being loosened. In the Swedish Patent 87 01949-3, a screw joint anchoring is described which affords an increased anchoring stability compared with previously known dental prostheses of this type. The screw joint anchoring is designed in such a manner that the dental prosthesis is unlikely loosen and has great capacity for transmitting stresses.

It is, however, not only important for the design of the screw and the distance element to be the best possible. The operational technique and the mounting of screw and distance element are also to be optimal. As a result of the torsional load, it is important for the distance screw to be tightened firmly. In this connection, the entire tightening torque comes to stress the screw which then risks loosening if special measures are not taken. According to the abovementioned Swedish Patent 87.01949-3, the distance element is provided with an inward, internal holder, in which fits one part of a double screwdriver adapted for the purpose fits. The other part of the double screwdriver is designed as a conventional screwdriver and fits the screwdriver slot in the head of the distance screw.

The distance element is arranged on the firmly rooted screw (the fixture) in such a manner that first the spacer is locked firmly against the fixture with the aid of the distance screw which is screwed down into a bore in the fixture with the aid of the double screwdriver, in doing which it is ensured that the legs of the tubular part engage with recesses in the spacer and the other part of the screwdriver is passed through the tubular part so that it engages in the screwdriver slot in the screw head of the distance screw. Upon mounting, it is endeavoured to apply to the screwdriver parts torques of the same size but in opposite directions. This can, however, be difficult to achieve in practice, especially in the case of high tightening torques.

The double screwdriver described above is of course applicable only in the case of manual tightening of the screw joint. There is, however, a desire to be able to carry out the tightening mechanically, that is to say with the drilling equipment available at the time of the dental operation. This facilitates the mounting for the dentist and also has the advantage that the tightening torque can be controlled.

SUMMARY OF THE INVENTION

The aim of this invention is to provide an apparatus which makes possible a mechanically controlled tightening of the screw joint of a dental implant without any torque being absorbed by the bone, so that the screw (the fixture) remains unstressed during mounting itself.

A preferred embodiment of the invention is shown schematically in the attached drawings in which

BRIEF DESCRIPTION OF THE DRAWINGS

FIG. 1 shows the hand-piece 1 of a drill of a known type which is used in connection with dental implant operations. The drill is used both for drilling of holes in the jawbone and for tightening of screw joints in the implant system. In this case, the drill is provided with a screwdriver 2 which is intended to interact with the screwdriver slot in the distance screw 3 which firmly locks the distance element against the upper part of the screw (the fixture), see also FIG. 3. In FIG. 1, the threaded part 4, which is intended to engage with an internally threaded recess in the upper part of the fixture for locking the distance element against the fixture, protrudes from the distance screw.

FIG. 1 also shows an apparatus 5 which interacts both with the distance element and with the hand-piece of the drill. The apparatus consists of a first, tubular part 6, the base of which connects to the distance element and through which the movable part of the drill, the screw-driver, runs, and a second, fork-shaped part 7 which interacts with the stationary part of the drill, the hand-piece 1.

Figure 3:
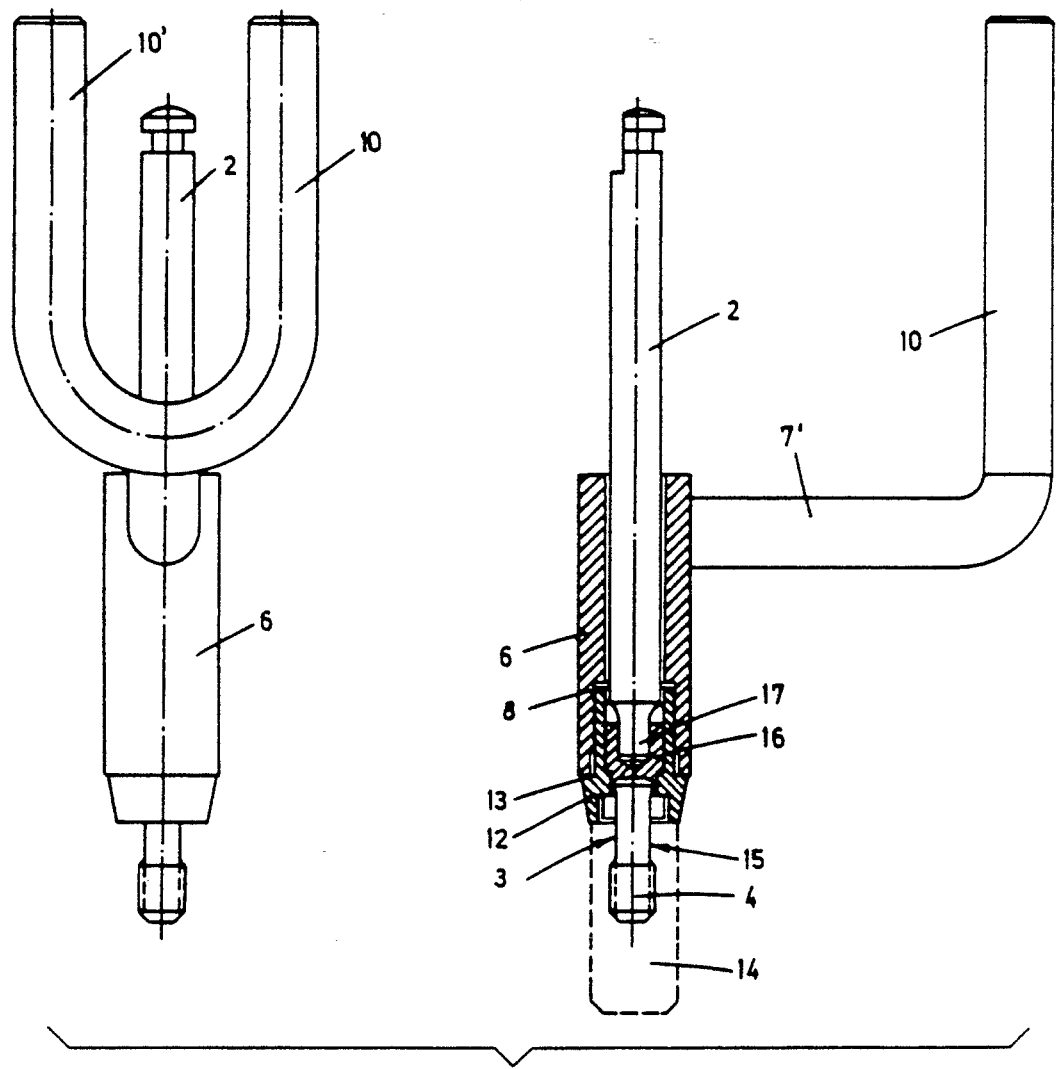
FIG. 3 is a second embodiment which also shows more closely how the apparatus interacts with the screwdriver of the drill and the distance element of the dental implant.

As more clearly seen from FIG. 3, the apparatus 5 functions as a holder at the time of tightening of the screw joint. The tightening torque does not come to stress the bone via the fixture since the fork-shaped part interacts with the hand-piece. An undesirable rotation of spacer and fixture is prevented by the legs of the fork-shaped part.

Figure 2:
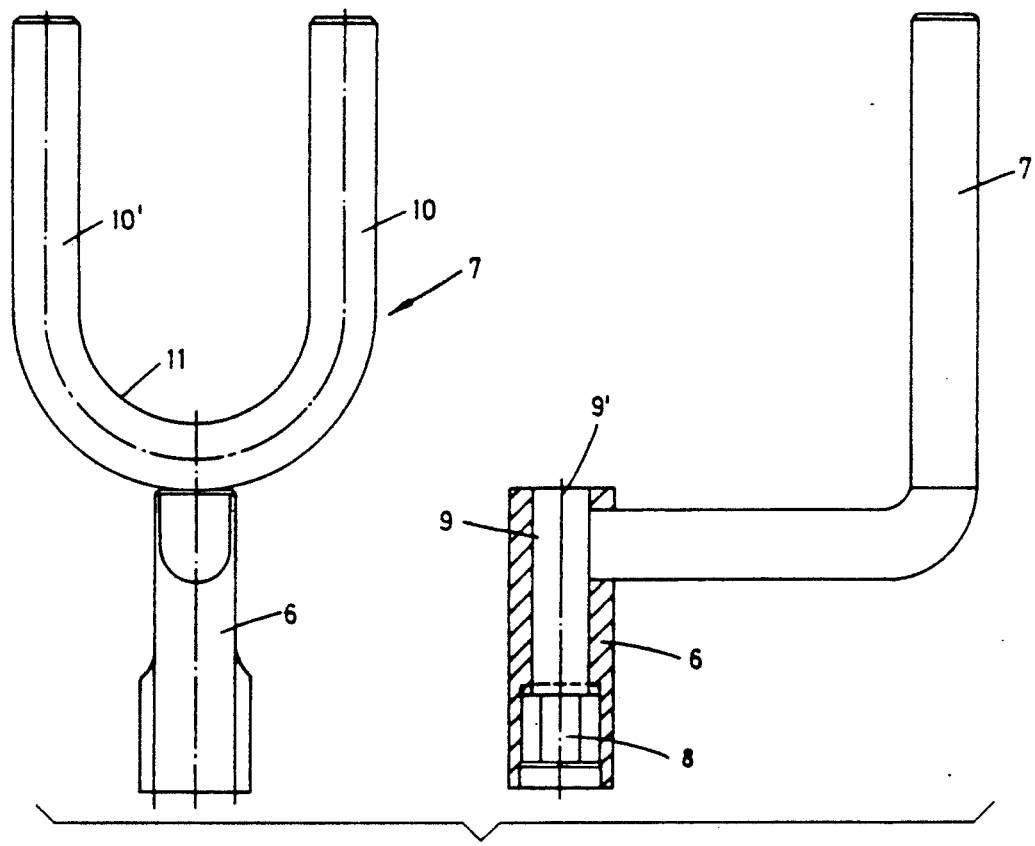
FIG. 2 shows a first embodiment of the present invention apparatus in two views.

In FIG. 2, a first embodiment of the apparatus 5 is shown. It comprises a first, tubular part 6, the base part of which is provided with an internal space 8 adapted to the spacer of the distance element in such a manner that the spacer is locked and cannot rotate in relation to the tubular part 6. The internal hole 9 has such a diameter that the screwdriver tool of the drill can rotate freely in this space.

Figure 1:
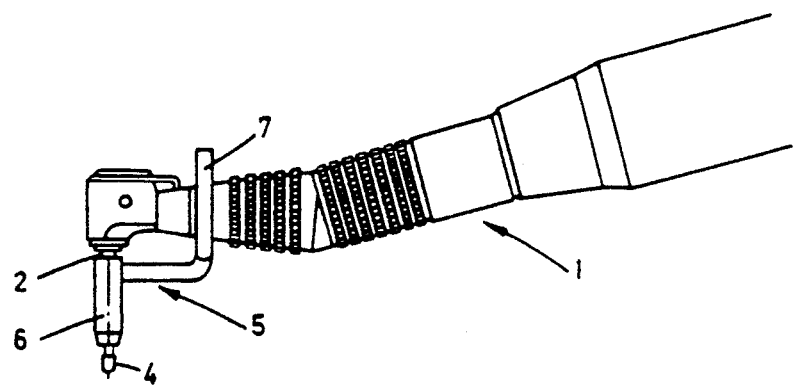
FIG. 1 shows the present invention together with a drill.

The tubular part 6 is provided with a fork 7, the base 7' of which extends essentially perpendicularly to the center line 9' of the tubular part, and the legs 10 of which are essentially parallel to the center line 9'. The fork is U-shaped and its bottom 11 forms a support for the hand-piece of the drill, and the legs 10, 10' are of such a length that they exceed the diameter of the hand-piece, see FIG. 2a and FIG. 1.

In FIG. 3, a second embodiment of the apparatus 5 according to the invention is shown. In this case is shown how the device 5 interacts, on the one hand, with the screwdriver tool 2 of the drill and, on the other hand, with the distance element of the dental implant, in the form of a spacer 12 and a distance screw 3. The end surface 13 of the tubular part 6 bears against the shoulder located on the spacer 12 and the recess 8 corresponds to the cylindrical, hexagonal upper part of the spacer so that a rotation of the spacer in relation to the tubular part 6 is prevented. The distance screw 3 is provided in a known manner with a lower threaded part 4 intended to engage with an internally threaded recess in the upper part of the fixture for locking of the spacer against the fixture 14 which has been marked with broken lines in the Figure. The distance screw also has a waist 15 and a screw head 16 with screwdriver slot 17, in which the screwdriver tool 2 of the drill engages. As mentioned above, the tightening torque does not impose stress the spacer 12, and consequently the fixture, since this torque is absorbed by the legs 10 of the fork.

The torque arising upon tightening, the screw tightening torque, gives rise to a reaction torque which in the case of normal tightening, tightening without holder, has to be conveyed via the hand. This torque then stresses the bone via the implant. With the present invention, the reaction torque does not have to be absorbed with the hand, but the hand-piece bears against one leg of the fork. In this manner, the reaction torque is transmitted from the hand-piece to the implant. As the tightening torque and the reaction torque are always of identical size but in opposite directions, this leads to the tissue surrounding the implant remaining unstressed.

The present invention is not limited to the embodiments which are shown in FIGS. 2 and 3. The important aspect is that the device is rotationally locked against the stationary part of the tightening tool (the drill). A fork with two legs is preferable for this locking since rotational locking in both directions can then be achieved and moreover provides a support and guide for the tightening tool. In certain cases, however, a single arm which extends from the tubular part and interacts with the tightening tool can be sufficient.

I claim:

1. A device for holding a tightening tool used for mechanical tightening of a screw joint in a bone-anchored dental implant without imposing stress upon the tissue surrounding the implant, said device comprising:

a first part adapted for receiving a movable part of said tightening tool, said first part being rotationally lockable with respect to the implant and a second part forming an arm which is rigidly connected to said first part and extends substantially perpendicularly thereto, said second part being also provided with a holding portion adapted for holding and rotationally locking a stationary part of the tightening tool such that interaction between said holding part and the stationary part of the tightening tool prevents transmission of the tightening torque through the implant to the surrounding tissue.

2. A device according to claim 1, wherein said first part includes a substantially tubular portion adapted for passing the movable part of the tightening tool therethrough.

3. A device according to claim 2, wherein said holding part adapted for interacting with the stationary part of the tightening tool includes a U-shaped fork-like member in which the stationary part of the tightening tool rests.

4. A device according to claim 2, wherein the base part of said tubular first part is provided with an internal portion adapted in shape to cooperate with a corresponding upper part of the dental implant for rotational locking of the dental implant with respect to said tubular part.

5. A device according to claim 4, wherein the dental implant includes a distance element and said internal portion of said tubular part cooperates with said distance element for rotationally locking of the distance element with respect to said tubular part.

6. A device according to claim 1, wherein said holding part adapted for interacting with the stationary part of the tightening tool includes a U-shaped fork-like member in which the stationary part of the tightening tool rests.

* * * * *